United States Patent
Park et al.

(10) Patent No.: US 8,809,390 B2
(45) Date of Patent: Aug. 19, 2014

(54) COMPOUND ACCELERATING SECRETION OF HUMAN-DERIVED ANTI-MICROBIAL PEPTIDE, METHOD FOR PREPARING SAME, AND COMPOSITION HAVING SAME AS ACTIVE INGREDIENT

(71) Applicant: Neopharm Co., Ltd., Daejeon (KR)

(72) Inventors: Byoeung-Deog Park, Cheongju-si (KR); Jong-Hwan Bae, Daejeon (KR); Se-Kyoo Jeong, Daejeon (KR); Hyoung-Sub Gwak, Daejeon (KR)

(73) Assignee: Neopharm Co., Ltd., Daejeon (KR)

( * ) Notice: Subject to any disclaimer, the term of this patent is extended or adjusted under 35 U.S.C. 154(b) by 0 days.

(21) Appl. No.: 13/779,080

(22) Filed: Feb. 27, 2013

(65) Prior Publication Data
US 2013/0190397 A1     Jul. 25, 2013

Related U.S. Application Data

(63) Continuation of application No. PCT/KR2010/005759, filed on Aug. 27, 2010.

(51) Int. Cl.
| | |
|---|---|
| *A01N 37/00* | (2006.01) |
| *A61K 31/21* | (2006.01) |
| *A01N 37/18* | (2006.01) |
| *A61K 31/16* | (2006.01) |
| *A61K 31/04* | (2006.01) |

(52) U.S. Cl.
USPC .......................... 514/506; 514/625; 514/741

(58) Field of Classification Search
None
See application file for complete search history.

(56) References Cited

FOREIGN PATENT DOCUMENTS

| GB | 2198042 A | * | 6/1988 |
|---|---|---|---|
| JP | 2004/059498 A | * | 2/2004 |
| WO | WO 9955330 A1 | * | 11/1999 |
| WO | WO 2009095485 A1 | * | 8/2009 |

OTHER PUBLICATIONS

Bastiat et al. Journal of Materials Chemistry 2008 (19) 3867-3877.*
Fincher et al. Journal of Pharmaceutical Sciences 1996 (85) 920-923.*
JP 2004/059498 A (machine translation).*

* cited by examiner

*Primary Examiner* — Jeffrey S. Lundgren
*Assistant Examiner* — Michael Schmitt
(74) *Attorney, Agent, or Firm* — Sughrue Mion, PLLC

(57) ABSTRACT

Disclosed is a compound having an acceleration effect on the secretion of human β-defensin, LL-37, which is a human-derived anti-microbial peptide, a method for preparing same, and a composition for accelerating the secretion of anti-microbial peptide having same as an active ingredient, and the compound and the composition using same of the present invention enhance the anti-microbial effect and the immunity control effect that the anti-microbial peptide has in the body by accelerating the secretion of the anti-microbial peptide in the body.

4 Claims, 7 Drawing Sheets

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: primer
<400> SEQUENCE: 1
gggcatgaac catgagaagt                                               20

<210> SEQ ID NO 2
<211> LENGTH: 20
<212> TYPE: DNA
<213> ORGANISM: Artificial Sequence
<220> FEATURE:
<223> OTHER INFORMATION: Primer
<400> SEQUENCE: 2
gtcttctggg tggcagtgat                                               20

<210> SEQ ID NO 3
<211> LENGTH: 21
<212> TYPE: DNA
<213> ORGANISM: Artificial Sequence
<220> FEATURE:
<223> OTHER INFORMATION: primer
<400> SEQUENCE: 3
ccagccatca gccatgaggg t                                             21

<210> SEQ ID NO 4
<211> LENGTH: 21
<212> TYPE: DNA
<213> ORGANISM: Artificial Sequence
<220> FEATURE:
<223> OTHER INFORMATION: Primer
<400> SEQUENCE: 4
ggagcccttt ctgaatccgc a                                             21

<210> SEQ ID NO 5
<211> LENGTH: 20
<212> TYPE: DNA
<213> ORGANISM: Artificial Sequence
<220> FEATURE:
<223> OTHER INFORMATION: primer
<400> SEQUENCE: 5
ttccaggtca tggaggaatc                                               20

<210> SEQ ID NO 6
<211> LENGTH: 20
<212> TYPE: DNA
<213> ORGANISM: Artificial Sequence
<220> FEATURE:
<223> OTHER INFORMATION: Primer
<400> SEQUENCE: 6
gagcacttgc cgatctgttc                                               20

<210> SEQ ID NO 7
<211> LENGTH: 20
<212> TYPE: DNA
<213> ORGANISM: Artificial Sequence

```
<220> FEATURE:
<223> OTHER INFORMATION: primer

<400> SEQUENCE: 7
gagaagggtg accgactcag                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
atgttcgtcc tcctcacagg                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tcggatgcta acctctaccg                                               20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gggtacaaga ttccgcaaaa                                               20
```

COMPOUND ACCELERATING SECRETION OF HUMAN-DERIVED ANTI-MICROBIAL PEPTIDE, METHOD FOR PREPARING SAME, AND COMPOSITION HAVING SAME AS ACTIVE INGREDIENT

CROSS REFERENCE TO RELATED APPLICATIONS

This application is a continuation application of PCT International Application No. PCT/KR2010/005759 filed Aug. 27, 2010, the contents of which are incorporated herein by reference in their entirety.

TECHNICAL FIELD

The following disclosure relates to a compound for promoting the secretion of human antimicrobial peptides, and more particularly, to a new compound for inducing direct or indirect expression of human β-defensin-2 and -3 and LL-37, which are human antimicrobial peptides, a method for preparing the same, and a composition comprising the same as an active ingredient.

BACKGROUND

Antimicrobial peptides are natural antimicrobial materials involved in innate immunity mechanisms in vivo, and low-molecular weight peptide materials that retain antimicrobial activities against various microorganisms including bacteria, fungi, and viruses and induce local biophylaxis and systemic immune response. The antimicrobial peptide generally has an amphipathic structure, and according to antimicrobial mechanism thereof, a cation part thereof binds to an anionic phospholipid included in a cell membrane of the microorganism to break the cell membrane of the microorganism.

Defensins are one of the antimicrobial peptides that have been most studied, and are largely classified into α-defensin and β-defensin depending on structural characteristics thereof. β-defensin is a peptide material that is expressed in mucous epithelium such as skin, lungs, organs, kidneys, reproductive organs, etc. Until now, 6 sorts of human β-defensins, human β-defensin-1 (hBD-1), human β-defensin-2 (hBD-2), human β-defensin-3 (hBD-3), human β-defensin-4 (hBD-4), human β-defensin-5 (hBD-5), and human β-defensin-6 (hBD-6) have been separated and identified. In particular, while hBD-1 is uniformly expressed in epidemic cells, hBD-2 is increasingly expressed at an infected region or a physically damaged region and has been known to play an important role in controlling a systemic immune response and an inflammatory response. In addition, it has been recently reported that hBD-3 is very highly expressed at skin lesion regions of psoriasis patients. In recent years, it has been recently known that β-defensins are involved in not only local phylaxis but also acquired immunity resulting from chemotactic migration of dendritic cells, T lymphocytes, monocytes, etc.

Cathelicidins have extensive antimicrobial activities and various immunomodulatory functions. LL-37, one of the human cathelicidin degradation products, has a α-helix structure, and has extensive antimicrobial activities and inflammation modulatory functions in vivo. In other words, LL-37 exhibits direct antimicrobial activities against bacteria, fungi, viruses, etc., and chemotaxis for neutrophil, mononuclear cells, and T cells, and induces proliferation of endotheliocyte. In particular, LL-37 existing in the skin does prompt defense at the time of penetration of foreign antigens, and thus has antigen inhibitory functions (Braff M H, Bardan A, Nizet V, et al. Cutaneous defense mechanisms by antimicrobial peptides. *J Invest Dermatol* (2005) 125, 9).

When physical damage or infection occurs in the skin, defensin and LL-37, which are antimicrobial peptides, are secreted to induce antimicrobial activity and a systemic immune response, and particularly induce differentiation and proliferation of epidermal keratinocytes, to thereby be involved in wound healing (Niyonsaba F, Ushio H, Nakano N, et al. Antimicrobial peptides human β-defensins promote epidermal keratinocyte migration, proliferation and production of proinflammatory cytokines and chemokines. *J Invest Dermatol* (2007) 127, 594). Also, study results have been recently reported that expression of β-defensin-2, LL-37, etc., which are antimicrobial peptides, decreased in the skin of patients with atopic dermatitis, which is a cause of high sensitivity to staphylococcus (Ong P Y, et al. Endogenous Antimicrobial Peptides and Skin Infections in Atopic Dermatitis. *The England Journal of Medicine* (2002) 347, 1151-1160).

Therefore, the antimicrobial peptides play important roles in primary defense and treatment against foreign sources of infection. In particular, the antimicrobial peptides is expression-induced in the skin, thereby primarily inhibiting infection of the skin and blocking penetration of foreign sources of infection by promoting the recovery of the damaged region, and thus, play important roles in protection of skin and maintenance of skin health.

The related art reported materials promoting the secretion of antimicrobial peptides in vivo. Korean Patent Laid-Open Publication No. 10-2006-0076775 discloses that various organic acids promote β-defensin secretion and International Patent Laid-Open Publication No. WO 0168085 discloses that amino acid, isoleucine, promotes defensin secretion. However, there are limitations in that some materials have unfavorable effects and other materials induce simultaneous secretion of inflammatory cytokines as well as antimicrobial peptides. For this reason, there have been demands for compounds having superior activity of promoting secretion of antimicrobial peptide and not inducing secretion of inflammatory cytokines.

The present inventors synthesized various materials in order to produce new materials for promoting antimicrobial peptides for a long time, and conducted experiments for activities thereof. As a result, the present inventors synthesized new compounds having excellent effects in promoting the secretion of human β-defensins and LL-37 in vivo, and completed the present invention.

SUMMARY

An embodiment of the present invention is directed to providing a new compound for promoting secretion of human antimicrobial peptide in vivo.

Another embodiment of the present invention is directed to providing a method for preparing the new compound for promoting secretion of human antimicrobial peptides in vivo.

Still another embodiment of the present invention is directed to providing a composition including the new compound for promoting secretion of human antimicrobial peptides in vivo as an active ingredient.

In one general aspect, there is provided a new compound for promoting secretion of human antimicrovial peptides in vivio represented by Chemical Formula (I) below:

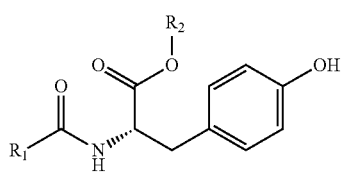

(I)

(wherein in Chemical Formula (I), $R_1$ is C1~C17 straight chain or branched alkyl, phenyl, or benzyl; and $R_2$ is hydrogen, methyl, or ethyl).

The compound of Chemical Formula (I) may have an effect of promoting secretion of human antimicrobial peptides, specifically, β-defensin and/or LL-37. Here, a more preferable compound may be a compound where $R_1$ is C5 straight chain alkyl and $R_2$ is methyl in the chemical formula (I) above, and may be represented by Chemical Formula (Ia) below.

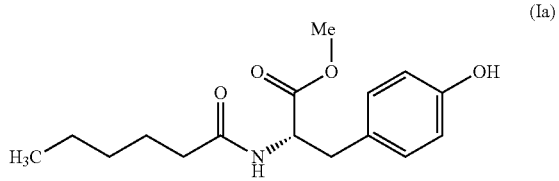 [SMILES: CCCCCC(=O)N[C@@H](Cc1ccc(O)cc1)C(=O)OC]

(Ia)

In another general aspect, there is provided a method for preparing a new compound for promoting secretion antimicrobial peptide in vivo, including:

(A) dissolving a compound of Chemical Formula (II) or hydrochloride thereof in an organic solvent in the presence of organic base; and (B) adding a compound of Chemical Formula (III) thereto at a reaction temperature of 0° C.~5° C., followed by stirring.

Compound of Chemical Formula (II)

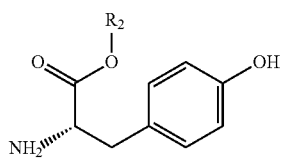

(II)

[wherein in Chemical Formula (II), $R_2$ is hydrogen, methyl, or ethyl]

Compound of Chemical Formula (III)

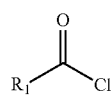

(III)

[wherein in Chemical Formula (III), $R_1$ is C1~C17 straight chain or branched alkyl, phenyl, or benzyl]

In still another general aspect, there is provided a composition for promoting secretion of antimicrobial peptides in vivo, the composition including the new compound of Chemical Formula (I) as an active ingredient.

Here, as the active ingredient, the compound of Chemical Formula (I) or Chemical Formula (Ia) may be contained at 0.001~90 wt %, and more preferably 0.001~50 wt %, in the composition.

Here, the formulation type of the composition may not be particularly limited as long as it is applicable for the human body including mucous membranes, such as, skin, respiratory tract, oral cavity, nasal cavity, or the like, as a local administration agent, and the composition may be prepared in a liquid phase, an emulsion phase, a suspension phase, a cream phase, an ointment phase, a gel phase, a jelly phase, or a spray phase.

Here, the formulation type of the composition may not be particularly limited as long as it is applicable for the human body as a systemic administration, and the composition may be prepared as an oral administration, an injection, or the like.

ADVANTAGEOUS EFFECTS

As set forth above, since the human antimicrobial peptides, defensin and LL-37, have prompt antimicrobial activities and are secreted in various tissues and organs of the body, including skin, the new compound of the present invention for promoting secretion of defensin and LL-37 and the composition including the same were administered for external use or for internal use, thereby exhibiting effective antimicrobial activities on various regions of the body while overcoming restricted administration paths, generation of antibiotic bacteria, safety problems, and the like, of the existing antimicrobial agents.

The material for promoting secretion of human defensin and LL-37 in vivo of the present invention can induce the promotion of secretion of β-defensin-2 and LL-37 in vivo at the applied region thereof, and thus enhance antimicrobial activities and immune functions, thereby improving bio-defense response. Therefore, the material for promoting secretion of antimicrobial peptides of the present invention is effective in prediction and treatment of syndromes resulting from infection by foreign antigens, such as bacteria, fungi, and viruses. In particular, the present invention induces an increase in antimicrobial peptides at a lesion region of atopic dermatitis where the antimicrobial peptides are reduced, and thus can obtain effective advantages in suppressing infection of the skin.

DETAILED DESCRIPTION OF EMBODIMENTS

Figure 1:
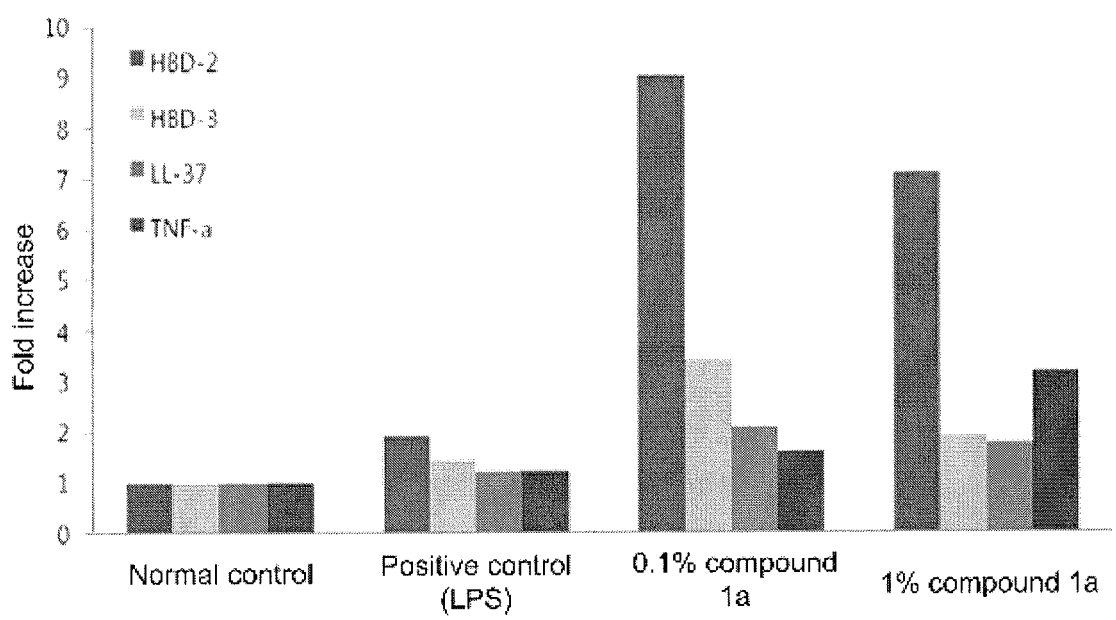
FIG. 1 is a graph showing expression degrees of human antimicrobial peptides, hBD-2 and LL-37 in vivo, by a compound of the present invention.

Hereinafter, a new compound for promoting secretion of human antimicrobial peptides in vivo according to the present invention will be described in detail.

A new compound for promoting secretion of human antimicrobial peptides in vivo has a structure of Chemical Formula (I) below:

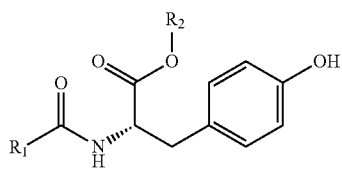

(I)

(wherein in Chemical Formula (I), $R_1$ is C1~C17 straight chain or branched alkyl, phenyl, or benzyl; and $R_2$ is hydrogen, methyl, or ethyl).

In the present invention, a compound where $R_1$ is C5 straight chain alkyl and $R_2$ is methyl in the chemical formula above, is more preferable, and represented by Chemical Formula (Ia) below:

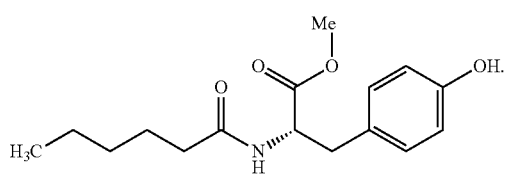

(Ia)

The compound of Chemical Formula (I) is prepared by the following method.

The compound of Chemical Formula (I) may be prepared by including: dissolving a compound of Chemical Formula (II) or hydrochloride thereof in an organic solvent in the presence of organic base; adding a compound of Chemical Formula (III) thereto at a reaction temperature of 0°~5° C., followed by stirring; and extracting, drying, and filtering the reacted material.

Compound of Chemical Formula (II)

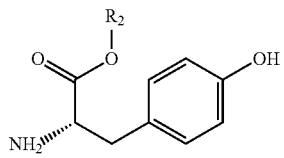

(II)

[Wherein in Chemical Formula (II), $R_2$ is hydrogen, methyl, or ethyl.]

Compound of Chemical Formula (III)

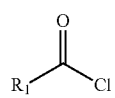

(III)

[Wherein in Chemical Formula (II), $R_1$ is $C_1$-$C_{17}$ straight chain or branched alkyl, phenyl, or benzyl.]

In the above reaction, the organic base is preferably selected from the group consisting of triethyl amine, diethyl amine, trimethyl amine, and dimethyl amine, and more preferable is trimethyl amine. In addition, the organic solvent used in the reaction is preferably selected from the group consisting of dichloro methane, N,N-dimethyl formamide, chloroform, acetonitrile, and acetone, and more preferable is dichloromethane. In the reaction, the step (B) is preferably carried out by stirring for 3~4 hours at 0° C.

The compound of Chemical Formula (Ia) as a representative compound of the compound of Chemical Formula (I) may be prepared as shown in the Reaction Scheme below.

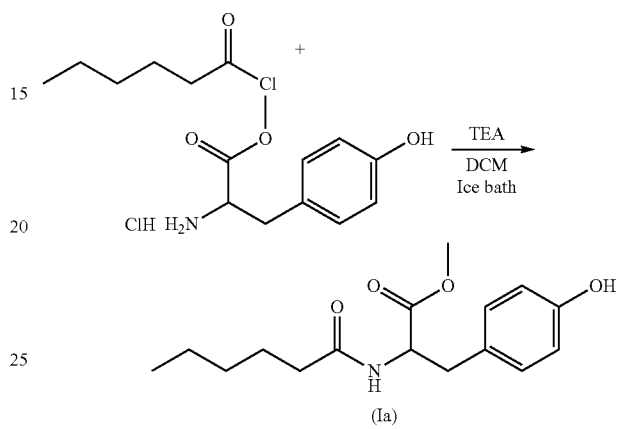

(Ia)

Dichloro methane (DCM) is added to (L)-tyrosine methyl ester HCl salt, and triethyl amine (TEA) is added thereto, thereby dissolving HCl salt. The reactor is temperature-lowered to 0° C. by using an ice bath, and hexanoyl chloride is slowly added, following by stirring for 3~4 hours. Water is added to the reacted material, followed by extraction with ethyl acetate. Drying over sodium sulfate followed by filtering is carried out. The solvent is removed from the filtrate by rotary evaporation, followed by solidification with hexane and ethyl acetate, thereby obtaining a white solid [Compound of Chemical Formula (Ia)].

As the experiment results confirming whether the thus synthesized compound of Chemical Formula (Ia) simulates secretion of β-defensin and cathelicidin, it can be seen that the compound of the present invention promotes secretion of β-defensin-2 and LL-37 in human cells that are cultured.

In addition, it can be confirmed that, by using the compound of Chemical Formula (Ia), expression of antimicrobial peptides is increased in the skin and anti-inflammatory efficacy and skin barrier function are improved as the result of application to an animal model with atopic dermatitis, and skin barrier recovery is significantly promoted as the result of experiments using an animal model with acute skin barrier disruption.

EXAMPLES

Hereinafter, the present invention will be described through the following examples and experimental examples, but the present invention is not limited to these examples.

Example 1

Preparation of (S)-Methyl 2-(hexanamido)-3-(4-hydroxyphenyl)propanoate 200 ml of dichloro methane (DCM) was added to (L)-tyrosine methyl ester HCl salt (23.16 g, 0.1 mol), and 28 ml of triethyl amine (TEA, 0.2 mol) was added thereto, thereby dissolving HCl salt. The reactor was temperature-lowered to 0° C. by using an ice bath, and hexanoyl chloride (13.8 ml, 0.1 mol) was slowly added, following by stirring for 3-4 hours. 200 ml of water was added to the reacted material, followed by extraction with 400 ml of ethyl acetate. Drying over sodium sulfate followed by filtering was carried out. The solvent was removed from the filtrate by rotary evaporation, followed by solidification with hexane and ethyl acetate, thereby obtaining a white solid (27.1 g, 92.5% yield) [hereinafter, referred to as Compound 1a].

mp: 96° C.

NMR (400 MHz $CDCl_3$) $^1H$: 0.873 (3H, t, $CH_3CH_2$), 1.261 (4H, m, $CH_3CH_2CH_2$), 1.584 (2H, m, $CH_2CH_2CH_2CH_2CO$), 2.175 (2H, t, $CH_2CH_2CO$), 2.955-3.118 (2H, dd, dd, $CHCH_2Ph$), 3.742 (3H, s, $OCH_3$), 4.883 (1H, m, $CH_2CH(NH)CO$), 5.922 (1H, d, NH), 6.720 (2H, d, CHC(OH)CH), 6.933 (2H, d, $CH(CH_2)CCH$)

Example 2

Preparation of (S)-Methyl 3-(4-hydroxyphenyl)-2-(octanamido)propanoate 200 ml of dichloro methane (DCM) was added to (L)-tyrosine methyl ester HCl salt (23.16 g, 0.1 mol), and 28 ml of triethyl amine (TEA, 0.2 mol) was added thereto, thereby dissolving HCl salt. The reactor was temperature-lowered to 0° C. by using an ice bath, and 16.6 ml of octanoyl chloride (0.1 mol) was slowly added, following by stirring for 3-4 hours. 200 ml of water was added to the reacted material, followed by extraction with 400 ml of ethyl acetate. Drying over sodium sulfate followed by filtering was carried out. The solvent was removed from the filtrate by rotary evaporation, followed by separation by column chromatograph using hexane and ethyl acetate (Hex:EA=2:1), thereby obtaining a white solid (30.1 g, 93.3% yield).

mp: 76° C.

NMR (400 MHz $CDCl_3$) $^1H$: 0.881 (3H, t, $CH_3CH_2$), 1.262 (8H, m, $CH_3CH_2CH_2CH_2CH_2$), 1.581 (2H, m, $CH_2CH_2CH_2CO$), 2.177 (2H, t, $CH_2CH_2CO$), 2.960-3.111 (2H, dd, dd, $CHCH_2Ph$), 3.740 (3H, s, $OCH_3$), 4.888 (1H, m, $CH_2CH(NH)CO$), 5.926 (1H, d, NH), 6.725 (2H, d, CHC(OH)CH), 6.931 (2H, d, $CH(CH_2)CCH$)

Example 3

Preparation of (S)-Methyl 2-(dodecanamido)-3-(4-hydroxyphenyl)propanoate 300 ml of dichloro methane (DCM) was added to (L)-tyrosine methyl ester HCl salt (23.16 g, 0.1 mol) and 28 ml of triethyl amine (TEA, 0.2 mol) was added thereto, thereby dissolving HCl salt. The reactor was temperature-lowered to 0° C. by using an ice bath, and 21.88 g of dodecanoyl chloride (0.1 mol) was slowly added, following by stirring for 3~4 hours. 200 ml of water was added to the reacted material, followed by extraction with 500 ml of ethyl acetate. Drying over sodium sulfate followed by filtering was carried out. The solvent was removed from the filtrate by rotary evaporation, followed by separation by column chromatograph using hexane and ethyl acetate (Hex:EA=2:1), thereby obtaining a white solid (34.2 g, 90.5% yield).

mp: 89° C.

NMR (400 MHz $CDCl_3$) $^1H$: 0.881 (3H, t, $CH_3CH_2$), 1.262 (16H, m, $(CH_2)_8$), 1.581 (2H, m, $CH_2CH_2CH_2CO$), 2.177 (2H, t, $CH_2CH_2CO$), 2.960~3.111 (2H, dd, dd, $CHCH_2Ph$), 3.740 (3H, s, $OCH_3$), 4.888 (1H, m, $CH_2CH(NH)CO$), 5.926 (1H, d, NH), 6.725 (2H, d, CHC(OH)CH), 6.931 (2H, d, $CH(CH_2)CCH$)

Example 4

Preparation of (S)-Methyl 3-(4-hydroxyphenyl)-2-(palmitamido)propanoate 300 ml of dichloro methane (DCM) was added to (L)-tyrosine methyl ester HCl salt (23.16 g, 0.1 mol), and 28 ml of triethyl amine (TEA, 0.2 mol) was added thereto, thereby dissolving HCl salt. The reactor was temperature-lowered to 0° C. by using an ice bath, and 27.49 g of palmitoyl chloride (0.1 mol) was slowly added, following by stirring for 3~4 hours. 200 ml of water was added to the reacted material, followed by extraction with 500 ml of ethyl acetate. Drying over sodium sulfate followed by filtering was carried out. The solvent was removed from the filtrate by rotary evaporation, followed by solidification with hexane and ethyl acetate, thereby obtaining a white solid (39.4 g, 90.8% yield).

mp: 100° C.

NMR (400 MHz $CDCl_3$) $^1H$: 0.881 (3H, t, $CH_3CH_2$), 1.262 (24H, m, $CH_3(CH_2)_{12}$), 1.581 (2H, m, $CH_2CH_2CH_2CO$), 2.177 (2H, t, $CH_2CH_2CO$), 2.960~3.111 (2H, dd, dd, $CHCH_2Ph$), 3.740 (3H, s, $OCH_3$), 4.888 (1H, m, $CH_2CH(NH)CO$), 5.926 (1H, d, NH), 6.725 (2H, d, CHC(OH)CH), 6.931 (2H, d, $CH(CH_2)CCH$)

Example 5

Preparation of (S)-Methyl 3-(4-hydroxyphenyl)-2-(phenylacetamido)propanoate 200 ml of dichloro methane (DCM) was added to (L)-tyrosine methyl ester HCl salt (23.16 g, 0.1 mol), and 28 ml of triethyl amine (TEA, 0.2 mol) was added thereto, thereby dissolving HCl salt. The reactor was temperature-lowered to 0° C. by using an ice bath, and 15.46 g of phenylacetyl chloride (0.1 mol) was slowly added, following by stirring for 3~4 hours. 200 ml of water was added to the reacted material, followed by extraction with 400 ml of ethyl acetate. Drying over sodium sulfate followed by filtering was carried out. The solvent was removed from the filtrate by rotary evaporation, followed by solidification with hexane and ethyl acetate, thereby obtaining a white solid (27.7 g, 88.1% yield).

mp: 101° C.

NMR (400 MHz $CDCl_3$) $^1H$: 2.852-3.032 (2H, dd, dd, $CHCH_2Ph$), 3.554 (2H, s, $PhCH_2CO$) 3.709 (3H, s, $OCH_3$), 4.837 (1H, m, $CH_2CH(NH)CO$), 5.917 (1H, d, NH), 6.628 (2H, d, CHC(OH)CH), 6.724 (2H, d, $CH(CH_2)CCH$), 7.155-7.348 (5H, m, $PhCH_2$)

Example 6

Production of Cream Formulation

A cream formulation having the following composition was produced by a general method for forming cream.

TABLE 1

| | Function | Ingredient | Weight (%) |
|---|---|---|---|
| Aqueous Phase | Antiseptic | Methyl paraben | 0.2 |

TABLE 1-continued

| | Function | Ingredient | Weight (%) |
|---|---|---|---|
| | Polymer | xanthan gum | 0.1 |
| | Moisturizer | Glycerine | 8.0 |
| | Purified Water | Water | 74.0 |
| Oil Phase | Fatty Acid | Stearic acid | 2.0 |
| | Higher Alcohol | Cetanol | 2.0 |
| | Wax | Bees wax | 2.0 |
| | Surfactant | POE(15) GMS | 2.5 |
| | Surfactant | POE(10) GMS | 1.0 |
| | Surfactant | GMS | 1.5 |
| | Oil | Macademia nut oil | 3.0 |
| | Oil | Squalane | 3.0 |
| | Antiseptic | Propyl paraben | 0.1 |
| | Active ingredient | Synthesized Material of Example 1 (Compound 1a) | 0.5 |
| Additive | Spice | Fragrance | 0.1 |

It was confirmed that cream produced from Example 6 had excellent storage stability and feeling of use.

In order to assess promotion of antimicrobial peptide secretion by using Compound 1a of Example 1, in vitro experiments were conducted.

Test Example 1

Promotion of Secretion of β-Defensin and LL-37

A medium containing 1% penicillin/streptomycin but not serum was used to culture human keratinocyte (HaCaT). The human keratinocyte was cultured in a 5% $CO_2$ incubator at 37° C. The cells were seeded in each well of a 6-well plate at $3 \times 10^5$ cells/well, and then cultured for 48 hours. 1.7 mM calcium chloride and the new material synthesized from Example 1 were added thereto, and the cells were allowed to culture for 24 hours.

For assessment, at least one untreated control and at least one positive control were used together. 2.5 ng/mL of lipopolysaccharides (LPS), which is known to promote expression of hBD-2 and LL-37, was used as the positive control, and was allowed to react. After the reaction was completed, a supernatant was collected, and then the cells were washed with phosphate buffer saline (PBS) and collected by using a trypsin-EDTA solution, and stored in a tube. 1 ml of a triazole reagent was added to extract mRNA. After reaction for 15 seconds at room temperature, 200 μl of chloroform was added. Centrifugal separation at 13,000 rpm was carried out for 10 minutes. The supernatant was transferred into another tube, and then 5000 of isopropanol was added thereto, followed by centrifugal separation at 13,000 rpm for 10 minutes. The precipitated RNA wash washed by using 70% ethanol. After washing was carried out two times, RNA was dissolved by using distilled water at the time of the third washing. The diluted RNA was analyzed at a wavelength between 260 nm and 280 nm, and quantitated.

The thus obtained RNA was subjected to RT-PCR procedure to obtain PCR results. For the RT-PCR, 2 μl of $MgCl_2$, 1 μl of RT buffer, 1 μl of dNTP mix, 0.25 μl of Rnase inhibitor, 0.5 μl of RTase, 0.5 μl of oligo dT, 3.75 μl of distilled water, and 2 μg of RNA were placed in the tube, and then were allowed to react. The RT-PCR conditions were 45° C. for 1 hour and 95° C. for 5 minutes. PCR was carried out for qualitative analysis on GAPDH, hBD-2 and -3, and LL-37. The used primers were obtained from the following documents (Kim J E, Kim B J, Jeong M S, et al, Expression and Modulation of LL-37 in Normal Human Keratinocytes HaCaT Cells and Inflammatory Skin Diseases. *J Korean Med Sci* (2005) 20, 649; Pernet I, Reymermier C, Guezennec A, et al, Calcium triggers beta-defensin (hBD-2 and hBD-3) and chemokine macrophage inflammatory protein-3 alpha (MIP-3alpha/CCL20) expression in monolayers of activated human keratinocytes. *Exp Dermatol* (2003) 12, 755).

The used primers are as follows.

```
GAPDH sense:
                                        (SEQ ID NO: 1)
5'-GGG CAT GAA CCA TGA GAA GT-3'

GAPDH antisense:
                                        (SEQ ID NO: 2)
5'-GTC TTC TGG GTG GCA GTG AT-3' hBD-2 sense:
                                        (SEQ ID NO: 3)
5'-CCA GCC ATC AGC CAT GAG GGT-3' hBD-2 antisense:
                                        (SEQ ID NO: 4)
5'-GGA GCC CTT TCT GAA TCC GCA-3' hBD-3 sense:
                                        (SEQ ID NO: 5)
5'-TTC CAG GTC ATG GAG GAA TC-3' hBD-3 antisense:
                                        (SEQ ID NO: 6)
5'-GAG CAC TTG CCG ATC TGT TC-3'

TNF-α sense:
                                        (SEQ ID NO: 7)
5'-GAG AAG GGT GAC CGA CTC AG-3'

TNF-α antisense:
                                        (SEQ ID NO: 8)
5'-ATG TTC GTC CTC CTC ACA GG-3'

LL-37 sense:
                                        (SEQ ID NO: 9)
5'-TCG GAT GCT AAC CTC TAC CG-3'

LL-37 antisense:
                                        (SEQ ID NO: 10)
5'-GGG TAC AAG ATT CCG CAA AA-3'
```

12.5 μl of PCR premix, 2 μl of primer sense (10 uM), 2 μl of primer antisense (10 uM), 1.5 μl of cDNA, and 7 μl of distilled water were inputted, and then PCR was carried out. PCR conditions of hBD-2 and -3 were 30 cycles of 94° C. for 30 seconds, 59° C. for 30 seconds, and 72° C. for 30 seconds, and then 72° C. for 10 minutes. PCR conditions of LL-37 were 30 cycles of 94° C. for 30 seconds, 60° C., for 30 seconds, and 72° C. for 30 seconds, and then 72° C. for 10 minutes. After amplification, the final products were mixed together, the final solution was loaded on an agaros gel containing a nucleic acid insertion visible under UV (such as, ethidium bromide), which is gelled at 1.5%. The sample was migrated and then read out under UV in a dark room, and digitally photographed. Photos of the gel were analyzed by image processing software which quantifies the band intensities. As basal levels of defensin and LL-37 expression (untreated control) were not detectable, antimicrobial peptide expression was detectable by using intensity ratios of the hBD-2/GAPDH, hBD-3/GAPDH, and LL-37/GAPDH bands in the positive control and sample-treated groups. Real-time PCR was carried out in order to more clarify these results. 5 μl of Sybergreen, 2 μl of primer sense (10 uM), 2 μl of primer antisense (10 uM), 1 μl of cDNA, and 1 μl of distilled water were inputted, and then the real-time PCR was carried out.

The results are shown in FIG. 1. As can be seen in FIG. 1, it can be seen that the compound of the present invention promotes the secretion of human β-defensin-2 and LL-37 from cultured human-derived cells.

Test Example 2

Recovery of Skin Barrier Damage

Skin barriers of nude mice were acutely damaged, and then effects of the new material represented in Example on recovery of acute skin barriers were assessed. D-Squame was used to induce skin barrier damage to left and right back regions of 6-8 week aged nude mice. Here, all the experimental groups were maintained to have no difference in trans epidermal water loss (TEWL) through measurement of the trans epidermal water loss (TEWL), and then vehicle (PEG:EtOH=7:3) and the new material represented in the example were coated thereon. The trans epidermal water loss (TEWL) was measured at the time of 0 h, 3 h, 6 h, and 24 h to confirm recovery of the skin barrier, and skin biopsies were conducted at the respective time, to thereby implement histological examination and other examinations.

Figure 2:
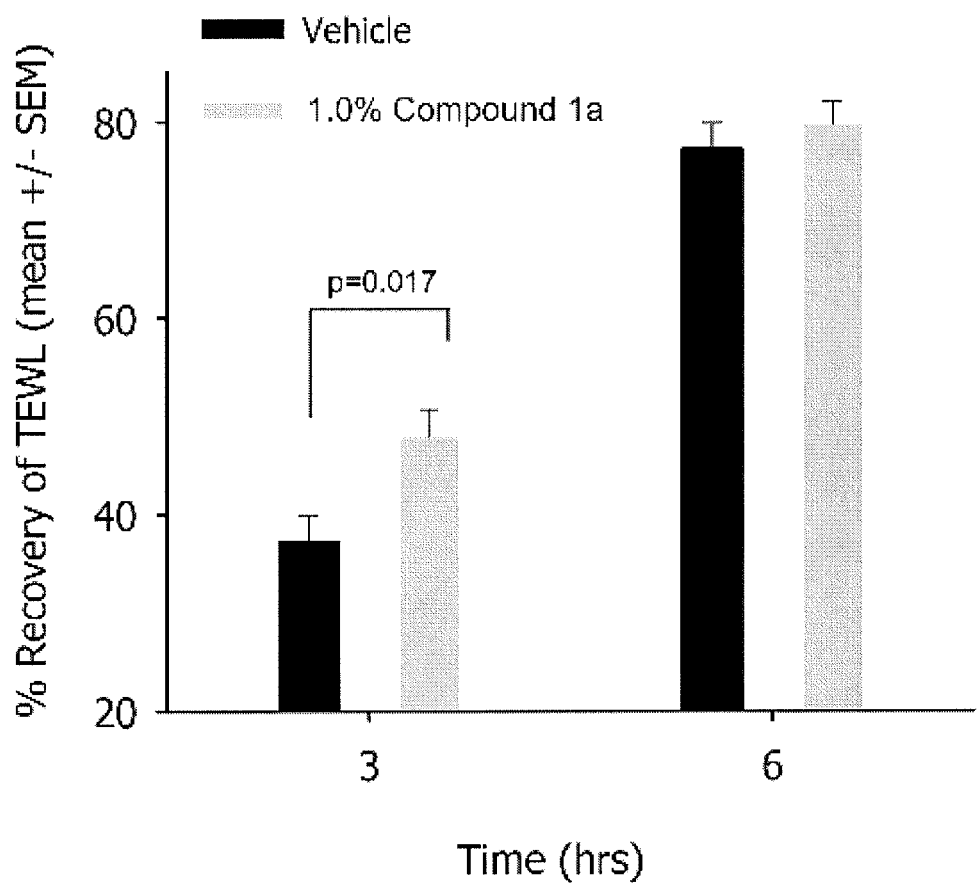
FIG. 2 is a graph showing skin barrier recovery capability in the mouse coated with the compound of the present invention.

The results are shown in FIG. 2. It can be confirmed from the results of FIG. 2 that the new compound of the present invention show significant results on the recovery of skin barrier damage.

Test Example 3

Efficacy Assessment on Animal Model with Atopic Dermatitis

An animal model with atopic dermatitis was constructed by coating the abdomens of 6-8 week aged nude mice with 5% oxazolone solution one time for percutaneous sensitization; after week, with 0.1% oxazolone solution every other day, six times, and 1% oxazolone solution every other day, four times. It has been reported that in the case of the animal model with atopic dermatitis using oxazolone, antimicrobial peptides were reduced in the skin (Man M-Q, Hatano Y, Lee S H, et al. Characterization of a hepten-induced, murine model with multiple features of atopic dermatitis: structural, immunologic, and biochemical changes following single versus multiple oxazolone challenges. *J Invest Dermatol* (2008) 128, 79-86). The skin of the animal model with atopic dermatitis constructed as above was coated with vehicle (PEG:EtOH=7:3) and Compound 1a of Example 1 diluted with the vehicle at a concentration of 0.1% once in the morning and in the afternoon for a total of four days. On the last day, thickness of the skin was measured. Corticosteroid based drug, Dexamethasone, which is an effective anti-inflammatory agent, was used as a positive control.

Figure 3:
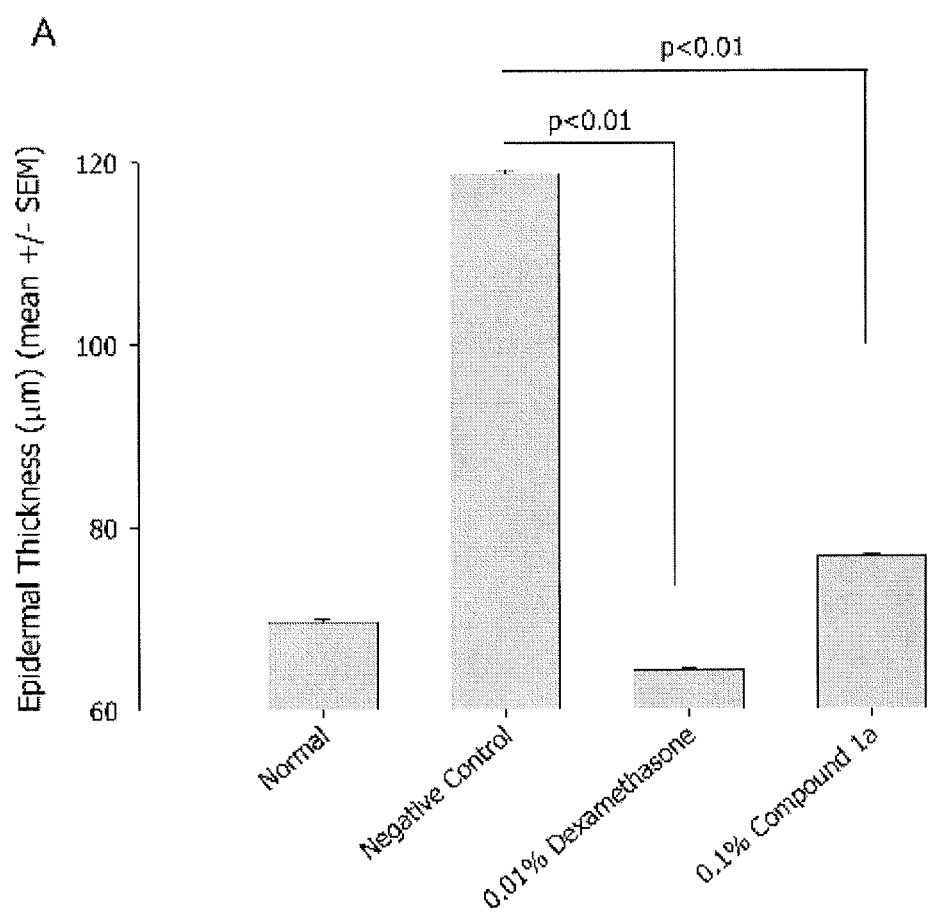
FIG. 3 is a graph showing anti-inflammatory efficacy of the compound of the present invention in an animal model with atopic dermatitis.

The obtained results are shown in FIG. 3. These results confirmed that the new material synthesized according to the example had an inflammatory effect in the animal model with atopic dermatitis.

Figure 4:
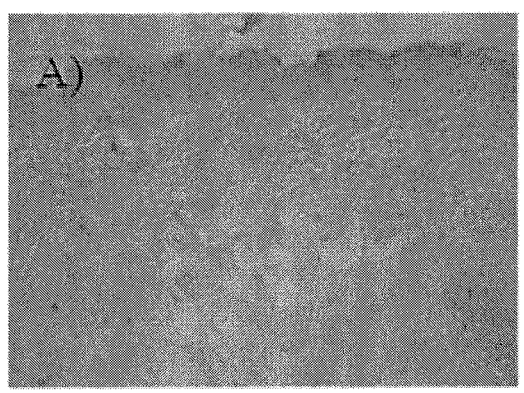
FIG. 4 is an image showing expression degrees of mouse antimicrobial peptide, CRAMP, which has a similar structure to human antimicrobial peptide, LL-37, in the corneum of the skin, when the compound of the present invention is coated on an atopic animal model.
Figure 4:
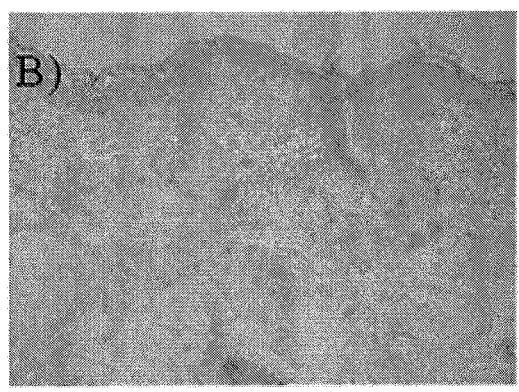
Figure 4:
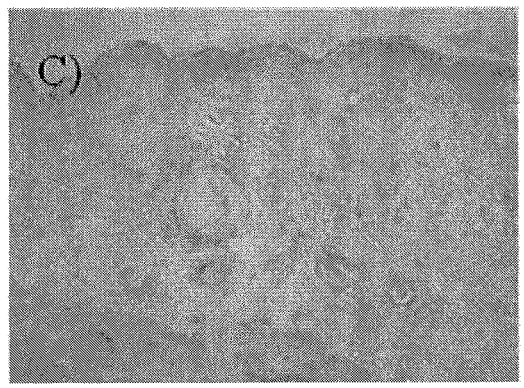
Figure 4:
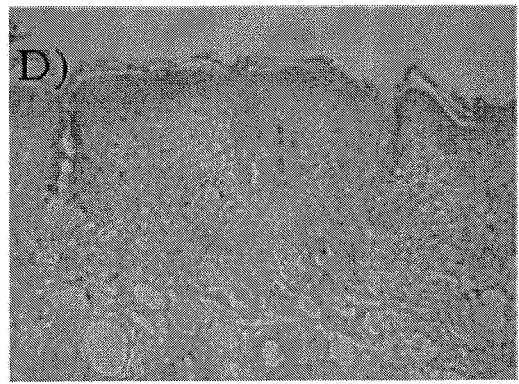

The new compound synthesized according to Example 1 was coated for four days, and then skin tissue biopsy was conducted to form a paraffin block. The tissue was allowed to adhere on the slide by using a paraffin cutter. After 500 μl of a peroxides blocking reagent was loaded, the reaction was carried out for 30 minutes. Washing with PBS solvent was carried out three times at a time interval of 5 minutes. After 500 μl of a peroxide blocking reagent was loaded, the reaction was carried out for 15 minutes. The first goat anti-mouse CRAMP was allowed to react at 25° C. for 30 minutes. The reaction using donkey anti-goat IgG-HRP as an antibody was carried out at 25° C. for 30 minutes. The reaction using DAB as a color forming agent was carried out for 10 minutes. After the reaction was completed, expression of CRAMP in the corneum of the skin was measured through a microscope. The obtained results were tabulated in Table 4. A), B), C), and D) of FIG. 4 show Normal, Negative control, 0.01% Dexamethasone, and 0.1% Compound 1a, respectively.

Figure 5:
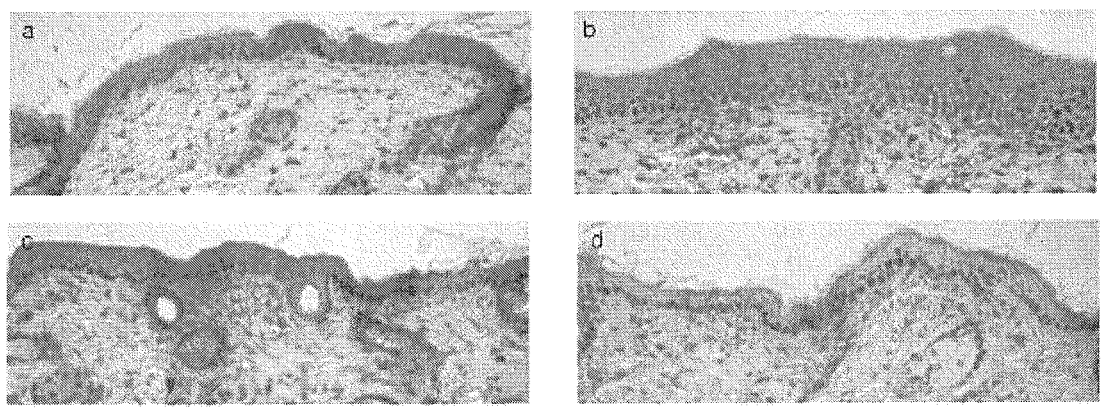
FIG. 5 is an image showing proliferation degrees of cells in the epidemic layer when the compound of the present invention is coated on an atopic animal model.
Figure 5:
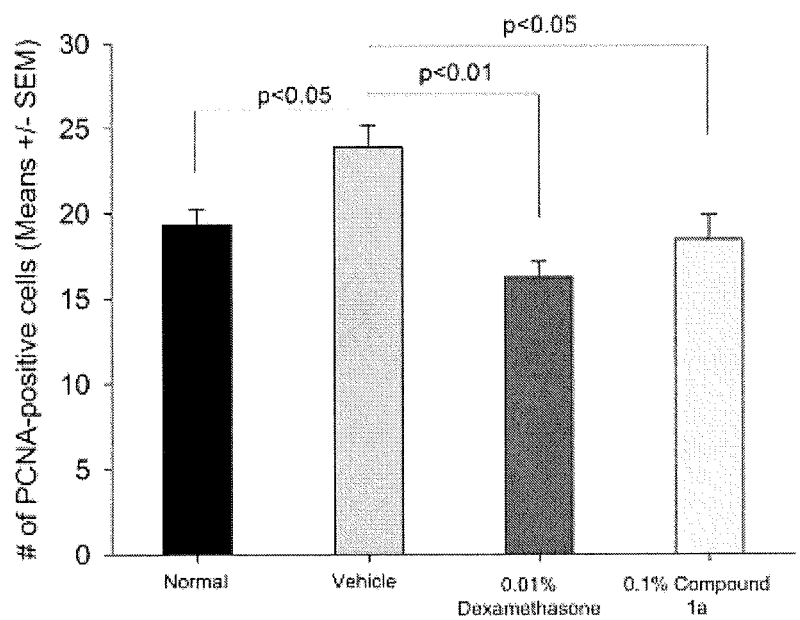

Another slide was used to measure proliferating cell nuclear antigen (PCNA). After 500 μl of a peroxides blocking reagent was loaded, the reaction was carried out for 30 minutes. Washing with PBS solvent was carried out three times at a time interval of 5 minutes. After 500 μl of a peroxides blocking reagent was loaded, the reaction was carried out for 15 minutes. The first rabbit anti-mouse PCNA was allowed to react out at 25° C. for 30 minutes. The reaction using donkey anti-rabbit IgG-HRP as an antibody was carried out at 25° C. for 30 minutes. The reaction using DAB as a color forming agent was carried out for 10 minutes. After the reaction was completed, proliferation of skin cells in the epidermis layer of the skin was measured through a microscope. The obtained results are shown in FIG. 5.

Figure 6:
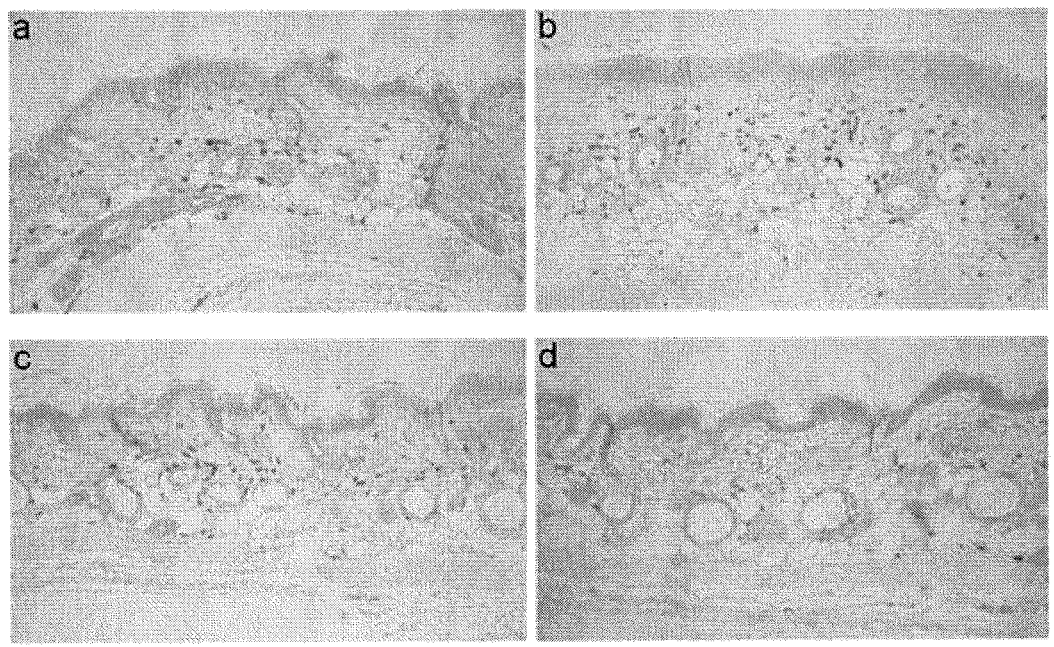
FIG. 6 is a graph showing mast cells when the compound of the present invention is coated on an atopic animal model.
Figure 6:
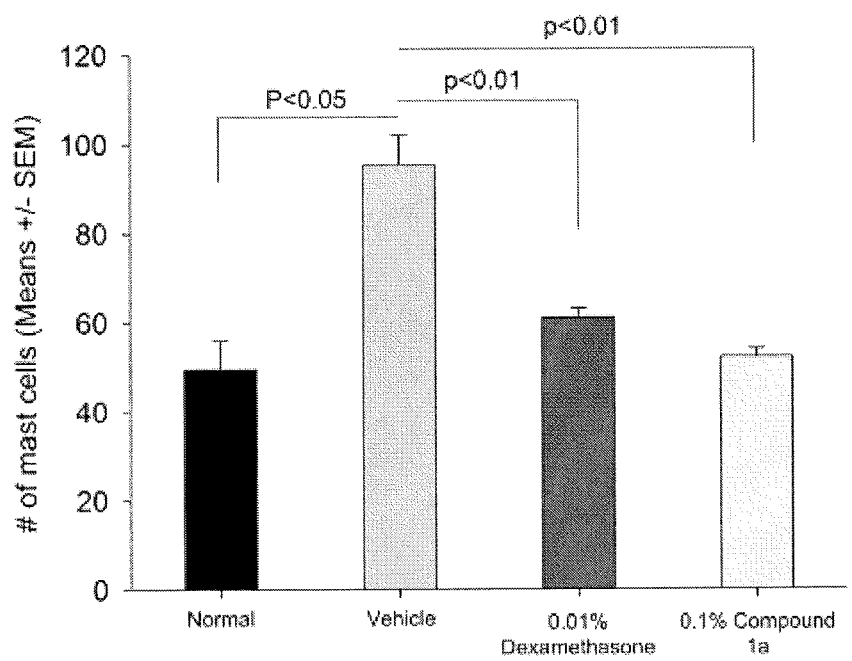

Another slide was used to measure mast cells. After paraffin was removed from the slide, the reaction in the potassium permanganate solution was carried out for 2 minutes. The slide was washed by using distilled water. The reaction in the potassium metabisulphite solution was carried out for 1 minute. The slide was washed by using distilled water for 3 minutes. The reaction in the acidified toluidine blue solution was carried out for 5 minutes. The slide was washed by using distilled water. After the reaction was completed, mast cells of the skin were measured through a microscope. The obtained results are shown in FIG. 6.

It can be seen from the above test results that the new compound of the present invention has superior inflammatory efficacy and significantly promotes improvement and recovery of skin barrier.

Test Example 4

Cytotoxicity

Figure 7:
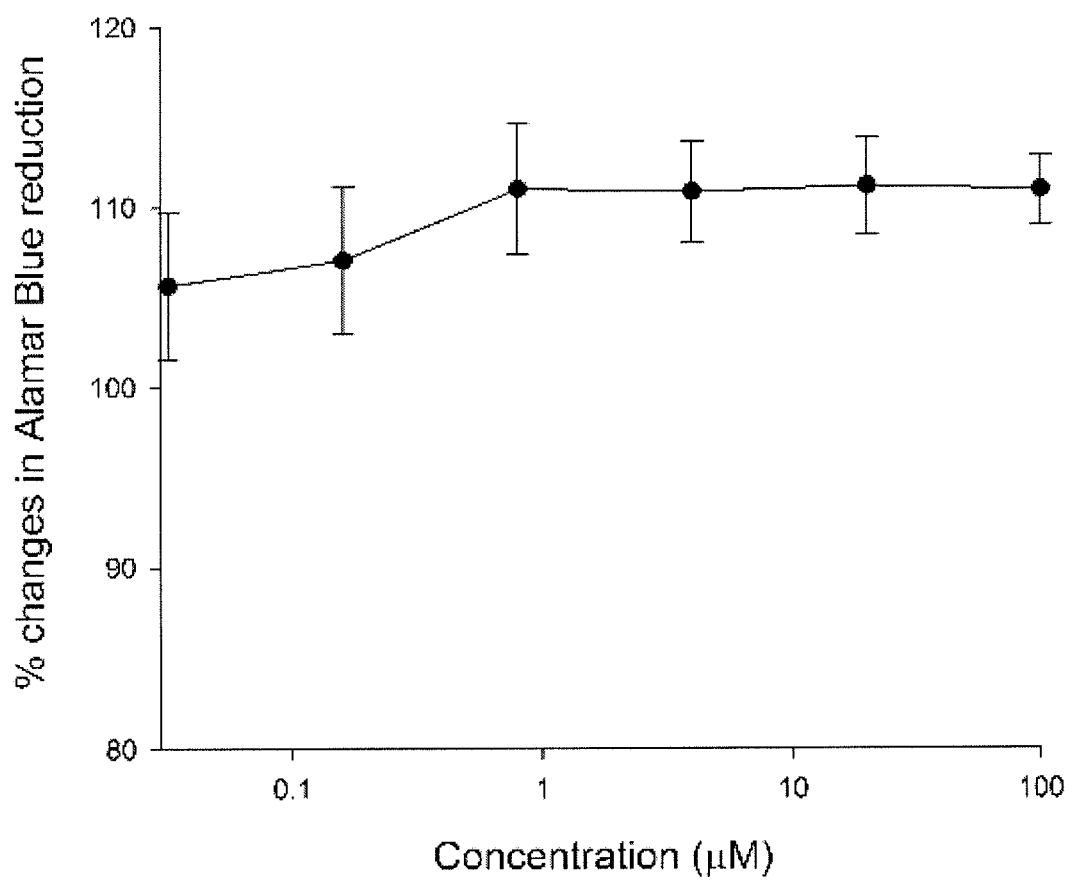
FIG. 7 is a graph showing cytotoxicity of the compound of the present invention.

A medium containing 1% penicillin/streptomycin but not serum was used to culture human keratinocyte (HaCaT). The human keratinocyte was cultured in a 5% CO2 incubator at 37° C. The cells were seeded in each well of a 96-well plate at $2.5 \times 10^4$ cells/well, and then cultured for 48 hours. The cells were further cultured for 24 hours by using a medium without serum. On the next day, the new material synthesized by the example was added at different concentrations thereof, and then the reaction was carried out for 24 hours. After four hours after the color forming reagent was put, apoptosis was measured at an absorbance of 590 nm. The obtained results are shown in FIG. 7.

It can be seen from the above test results that the new compound of the present invention has also no problems in view of stability.

INDUSTRIAL APPLICABILITY

The present invention is directed to an industrially applicable novel compound capable of inducing direct or indirect expression of human β-defensin-2 and -3 and LL-37, which are human antimicrobial peptides, a method for preparing the same, and a composition comprising the same as an active ingredient.

What is claimed is:

1. A pharmaceutical composition comprising a compound of Chemical Formula (I):

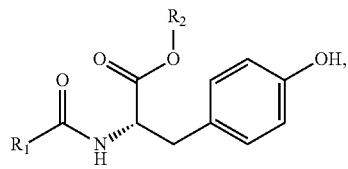

(I)

wherein $R_1$ is C5 or C7 straight chain alkyl; and $R_2$ is methyl, as an active ingredient.

2. The composition of claim 1, wherein the compound is contained in an amount of 0.001-90 wt % based on the total weight of the composition.

3. The composition of claim 1, which is in a formulation form selected from the group consisting of a liquid phase, an emulsion phase, a suspension phase, a cream phase, an ointment phase, a gel phase, a jelly phase, and a spray phase.

4. The composition of claim 1, which is in a formulation form selected from the group consisting of a tablet, a liquid, a powder, and an injection.

* * * * *